(12) United States Patent
Garner et al.

(10) Patent No.: US 11,198,004 B2
(45) Date of Patent: Dec. 14, 2021

(54) GOAL-DRIVEN WORKFLOW FOR CARDIAC ARRHYTHMIA TREATMENT

(71) Applicant: Biosense Webster (Israel) Ltd., Yokneam (IL)

(72) Inventors: John Brian Garner, Springfield, MO (US); Inna Yarin, Yokneam Illit (IL); Yaniv Ben Zrihem, Binyamina (IL)

(73) Assignee: BIOSENSE WEBSTER (ISRAEL) LTD., Yokneam (IL)

( * ) Notice: Subject to any disclaimer, the term of this patent is extended or adjusted under 35 U.S.C. 154(b) by 54 days.

(21) Appl. No.: 16/381,299

(22) Filed: Apr. 11, 2019

(65) Prior Publication Data

US 2020/0324118 A1 Oct. 15, 2020

(51) Int. Cl.
| | |
|---|---|
| *A61N 1/36* | (2006.01) |
| *A61B 5/024* | (2006.01) |
| *A61N 1/365* | (2006.01) |
| *A61N 1/37* | (2006.01) |
| *A61B 5/316* | (2021.01) |
| *A61B 5/363* | (2021.01) |

(52) U.S. Cl.
CPC ...... *A61N 1/36135* (2013.01); *A61B 5/02405* (2013.01); *A61B 5/316* (2021.01); *A61B 5/363* (2021.01); *A61N 1/36592* (2013.01); *A61N 1/3702* (2013.01); *A61N 1/371* (2013.01)

(58) Field of Classification Search
CPC ............ A61N 1/36135; A61N 1/36592; A61N 1/3702; A61N 1/371; A61B 5/02405; A61B 5/04012; A61B 5/0464
See application file for complete search history.

(56) References Cited

U.S. PATENT DOCUMENTS

| | | |
|---|---|---|
| 5,991,660 A | 11/1999 | Goyal |
| 7,907,994 B2 | 3/2011 | Stolarski et al. |
| 9,050,011 B2 | 6/2015 | Rubinstein et al. |
| (Continued) | | |

OTHER PUBLICATIONS

G.D. Veenhuyzen et al. in "Diagnostic Utility for Supraventricular Tachycardia," Indian Pacing Electrophysiology Journal, 8(1): pp. 51-65, (2008).

(Continued)

*Primary Examiner* — Lindsey G Wehrheim
(74) *Attorney, Agent, or Firm* — Notaro, Michalos & Zaccaria P.C.

(57) ABSTRACT

A system includes a memory and a processor. The memory is configured to store a definition of a cardiac pacing protocol. The processor is configured to (a) receive the stored definition of the cardiac pacing protocol, (b) in accordance with the pacing protocol, to automatically pace from an intracardiac location and to acquire respective sensed ECG signals, (c) based on one or more prespecified criteria for validity of the sensed ECG data, automatically accept or reject the sensed ECG signals, (d) based on one or more prespecified criteria for identification of an arrhythmia, identify the intracardiac location as an arrhythmogenic focus or pathway, (e) overlay the identified intracardiac location an electrophysiological (EP) map, and (f) subsequently identify or reject a new intracardiac location as an arrhythmogenic focus or pathway and overlay the new location on the EP map when pacing again from the new intracardiac location.

18 Claims, 3 Drawing Sheets

(56) References Cited

U.S. PATENT DOCUMENTS

| | | | |
|---|---|---|---|
| 10,149,626 B1* | 12/2018 | Boveja | A61B 5/0422 |
| 2010/0305433 A1 | 12/2010 | Harlev et al. | |
| 2012/0289846 A1* | 11/2012 | Zhang | A61B 5/0464 |
| | | | 600/515 |
| 2014/0005563 A1* | 1/2014 | Ramanathan | A61B 5/044 |
| | | | 600/523 |
| 2014/0200473 A1 | 7/2014 | Zeng et al. | |
| 2015/0216438 A1* | 8/2015 | Bokan | A61B 5/02405 |
| | | | 600/515 |
| 2017/0209696 A1* | 7/2017 | Kaiser | A61N 1/36514 |
| 2019/0008404 A1 | 1/2019 | Severino | |

OTHER PUBLICATIONS

EP 20169368.6-1126—Extended European Search Report dated Oct. 9, 2020.

\* cited by examiner

GOAL-DRIVEN WORKFLOW FOR CARDIAC ARRHYTHMIA TREATMENT

FIELD OF THE INVENTION

The present invention relates generally to electroanatomical mapping, and particularly to cardiac electroanatomical mapping.

BACKGROUND OF THE INVENTION

Cardiac mapping procedures for identifying potential sources of arrhythmia in a heart tissue were previously proposed in the patent literature. For example, U.S. Pat. No. 7,907,994 describes ventricular tachycardia signals that are induced in a living subject. Pace-mapped signals are then obtained from multiple points within the ventricle, and automatically compared numerically with the induced signals. Recognition of a high degree of cross correlation between the induced signals and one or more of the pace-mapped signals identifies arrhythmogenic foci or pathways, which may then be ablated, so that the arrhythmia becomes non-inducible.

As another example, U.S. Patent Application Publication 2014/0200473 describes a method that can determine one or more origins of focal activation. The method can include computing phase for the electrical signals at a plurality of nodes distributed across a geometric surface based on the electrical data across time. The method can determine whether or not a given candidate node of the plurality of nodes is a focal point based on the analyzing the computed phase and magnitude of the given candidate node. A graphical map can be generated to visualize focal points detected on the geometric surface.

SUMMARY OF THE INVENTION

Example embodiments of the present invention that are described hereinafter provide an automated workflow for cardiac pacing using one or more catheters, the workflow including a goal-driven algorithm that is capable of decision-making according to type and presets of pacing procedure, and the responses of the heart to such pacing, so as to increase procedure efficiency and success rate.

An embodiment of the present invention provides a system including a memory and a processor. The memory is configured to store a definition of a cardiac pacing protocol. The processor is configured to (a) receive the stored definition of the cardiac pacing protocol, (b) automatically control one or more probes in a heart of a patient, in accordance with the pacing protocol, to automatically pace from an intracardiac location and to acquire respective sensed electrocardiogram (ECG) signals, (c) based on one or more prespecified criteria for validity of the sensed ECG data, automatically accept or reject the sensed ECG signals, (d) based on one or more prespecified criteria for identification of an arrhythmia, identify or reject the intracardiac location as an arrhythmogenic focus or pathway, (e) overlay the identified intracardiac location on an electrophysiological (EP) map, and (f) subsequently identify a new intracardiac location as an arrhythmogenic focus or pathway and overlay the new location on the EP map when pacing again from the new intracardiac location.

In some embodiments, the definition includes at least a pacing sequence.

In some embodiments, the processor is further configured to visually indicate qualitative or quantitative results obtained from pacing at each paced intracardiac location to a user on the EP map.

In an embodiment, the pacing protocol specifies the one or more criteria for validity of the sensed ECG and/or intracardiac signal data, including a comparison of paced cycle length (PCL) to tachycardia cycle length (TCL) in the sensed signals.

In another embodiment, the pacing protocol specifies the one or more criteria for identification of a location as an arrhythmogenic focus or pathway, including one of: a comparison of tachycardia cycle length (TCL) to post-pacing interval (PPI) in a same ECG or intracardiac signal; and a a comparison of time lapse between pacing signal to a resulting body surface or intracardiac ECG signal with time lapse between one or more following pacing signals and respective resulting body surface or intracardiac ECG signals.

In an embodiment, the processor is configured to identify a location as an arrhythmogenic focus or pathway by identifying a location in a direction that leads towards lower PPI-TCL values, or lower difference in time lapse values.

In some embodiments, the pacing protocol specifies the one or more criteria for validity of the sensed ECG data, including comparison of time lapse values In some embodiments, the pacing protocol specifies the one or more criteria for identification of a location as an arrhythmogenic focus or pathway, including identifying concealed and/or manifested fusion in a sensed ECG signal. In an embodiment, the processor is configured to measure the intracardiac paced location using a position tracking system.

In another embodiment, the processor is configured to store the definition of the cardiac pacing protocol by at least one of saving, importing, and exporting of the pacing protocol.

There is additionally provided, in accordance with an embodiment of the present invention, a computer-implemented method, including, in a processor, receiving a definition of a cardiac pacing protocol. Using the processor, one or more probes in a heart of a patient are automatically controlled in accordance with the pacing protocol, to automatically pace from an intracardiac location and to acquire respective sensed ECG signals. Based on one or more prespecified criteria for validity of the sensed ECG data, the sensed ECG signals are automatically accepted or rejected. Based on one or more prespecified criteria for identification of an arrhythmia, the intracardiac location is identified an arrhythmogenic focus or pathway, or rejected as not being such a focus. The identified intracardiac cardiac location is overlaid on an electrophysiological (EP) map, and subsequently a new intracardiac location is identified as an arrhythmogenic focus or pathway and the new location is overlaid on the EP map when pacing again from the new intracardiac location.

The present invention will be more fully understood from the following detailed description of the embodiments thereof, taken together with the drawings in which:

DETAILED DESCRIPTION OF EMBODIMENTS

Overview

Figure 1:
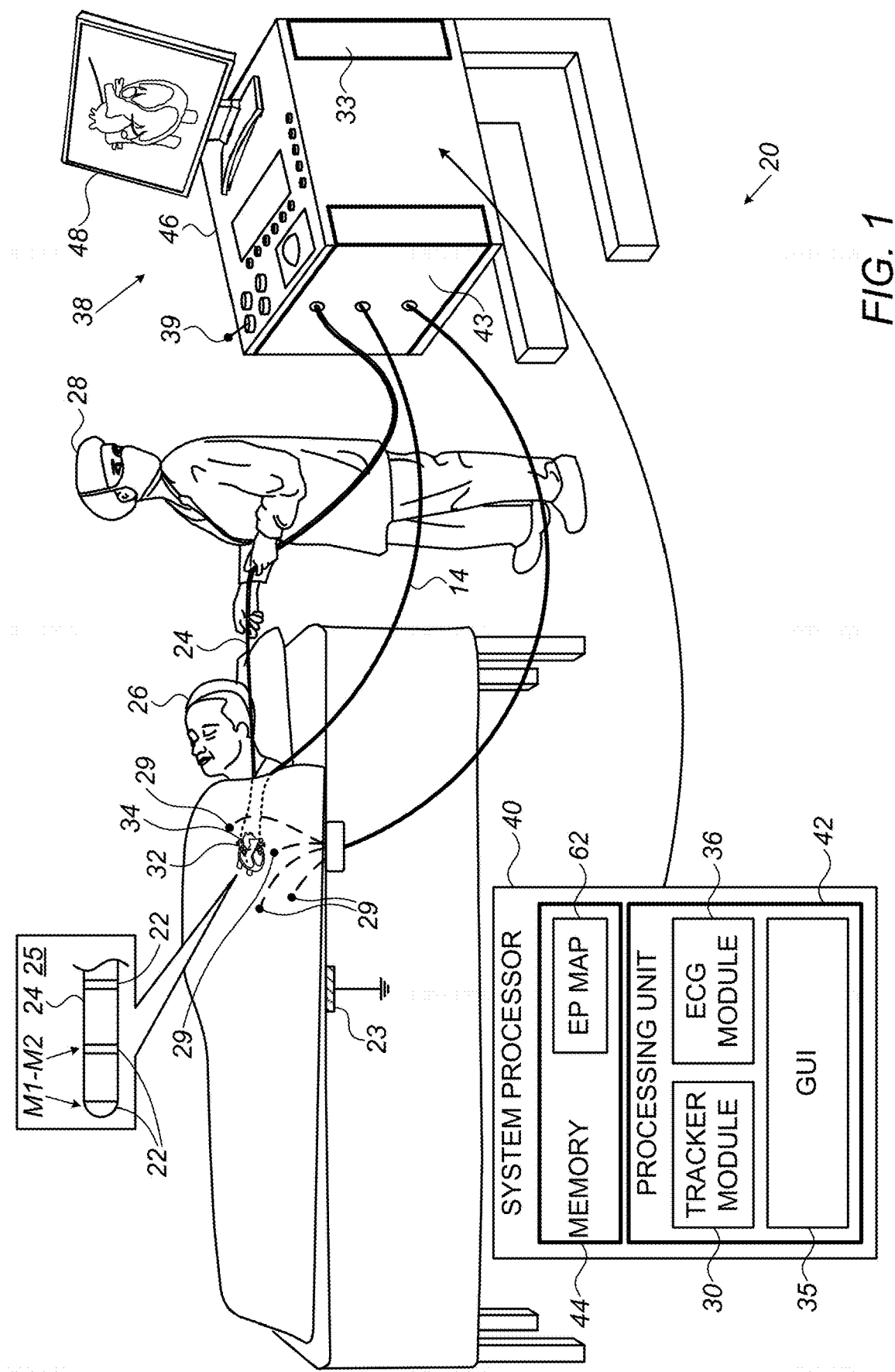
FIG. 1 is a schematic, pictorial illustration of a cardiac 3D navigation, electrophysiological (EP) diagnostics system, comprising a radiofrequency (RF) ablation sub-system, in accordance with an embodiment of the present invention.

Cardiac arrhythmia, which is defined as a variation from the normal heart sinus rhythm, may belong to several categories. One category is characterized by rapid and/or erratic electrophysiological (EP) pulses originating from one or more focal locations within the heart tissue. Another category is characterized by repetitive looping of electrical activity through one or more portions of heart tissue. Examples of the first category are focal arrhythmias, and of the second category are reentrant arrhythmias.

One possible method to find a location from which a focal arrhythmia originates, or through which a reentry arrhythmia propagates, is to stimulate selected locations of the cardiac tissues of a patient with bi-polar or unipolar electrical signals. Such stimulation, which may be done using electrodes on a catheter, may induce an electrocardiogram (ECG) signal pattern that meets one or more criteria for identification of a stimulated location as an arrhythmogenic focus or pathway, or conversely excludes such a site as originating or participating in the arrhythmia.

The underlying assumption is that treating such arrhythmogenic location (i.e., a location which is an arrhythmogenic focus or pathway), for example by ablating the location, is likely to reduce or eliminate the arrhythmia in question. The invasive diagnostic procedure described above is called a "pacing maneuver". Pacing maneuvers are usually a lengthy process, as they often have to be repeated manually over numerous locations inside the heart to achieve sufficient diagnostic information to allow a properly targeted ablation.

Embodiments of the present invention that are described hereinafter provide an automated workflow for cardiac pacing maneuvers using one or more catheters. The disclosed technique comprises a decision-making goal-driven algorithm that integrates separate pacing functionalities that would otherwise require tedious manual involvement from a physician. Furthermore, the disclosed technique saves the physician the mental fatigue of repeated decision-making otherwise required during a typical pacing maneuver set. Such laborious manual decision-making may result in an inconclusive or incorrect result of the pacing procedure, from which the physician may fail to identify correctly the target location needing treatment.

In some embodiments, at a beginning of the disclosed automated cardiac pacing procedure, the physician selects a pacing protocol according to type of arrhythmia in question. The protocol comprises the following parameters: (i) intracardiac locations for pacing, and for sensing resulting ECG signals, (ii) stimulation sequence and waveform, (iii) monitored parameters, (iv) acceptance criteria of data validity, and (v) criteria for verification that a diagnostic goal of the disclosed automated workflow has been achieved.

Examples of stimulation sequence and waveform parameters include duration of stimulation, and signal frequency, duty cycle and amplitude.

The examples that are listed below are for a certain possible procedure that the disclosed algorithm can perform. In general, multiple procedures can use the disclosed algorithm, with necessary changes made to parameters such as acceptance criteria.

By way of example, for a reentrant type of arrhythmia in question, acceptance criteria for use with an algorithm to decide whether a set of sensed ECG data is valid or not, may include the paced cycle length (PCL). In an embodiment, an algorithm checks if periodicity of ECG or intracardiac signals sensed during pacing have reached the PCL, an instant which the disclosed algorithm uses for stopping pacing and starting sensing of the response signals. If PCL was not reached in all target electrodes or sensed signals, the algorithm returns to the next stimulation in a preplanned sequence or instructs moving the pacing catheter to a next pre-defined pacing location. However, other acceptance criteria may be used with other types of arrhythmia in question.

In another embodiment, the algorithm stops the pacing after the processor determining ECG or intracardiac signals sensed during pacing have reached PCL (also named herein "activation capture") in all relevant channels. A validated capture means pacing is validated as successfully achieved. A subsequent analysis, required for verifying of the capture in a post-paced sensed ECG signal is described below. Alternatively, the algorithm stops the pacing after a certain time period (i.e., duration of stimulation or number of delivered pacing stimuli) has passed.

In an embodiment, the physician may change any preset parameter and save the newly resulting protocol in a memory. Accordingly, he will have the ability to export and import new automatic pacing protocols and share them among colleagues or on another system.

In another embodiment, the disclosed automatic workflow is configured to utilize guided placement of the one or more of the catheters. For example, the workflow applies magnetic and/or electrical position tracking of a catheter to guide catheter placement. Furthermore, a processor may use an algorithm, which the workflow automatically calls, to register the tracked position with an anatomical map of at least a portion of the heart.

In an embodiment, the disclosed workflow is configured to utilize catheter positioning and repositioning that is performed fully automatically, for example, using a processor controlled robotic catheter sub-system or magnetic catheter manipulation system.

In an embodiment, identifying a location as an arrhythmogenic focus or pathway comprises identifying a location in a direction that leads towards minimal or maximal values of PPI-TCL values, or towards minimal or maximal differences in time laps values, the differences defined by time lapse between pacing signal to a resulting body surface or intracardiac ECG signal versus time lapse between one or more following pacing signals and respective resulting body surface or intracardiac ECG signals.

In some embodiments, the automatic workflow applies pacing signals from a single pair of electrodes of a pacing and ablation catheter, the electrodes being the two most distal electrodes and named herein after "M1-M2," as further described below, or unipolar pacing from the most distal electrode (M1) to an indifferent electrode within or attached to the patient's body. In such case, except for the initial stimulation routing (to the chosen electrodes), no further stimulation routing is required.

In another embodiment, the disclosed automated pacing workflow may instruct performing stimulation from multiple electrode-pairs, using automatic stimulation routing feature to switch between the different electrode-pairs. Alternatively, such pacing may be in unipolar fashion from a single electrode at a time to an indifferent electrode within or attached to the patient's body. An example of a procedure that may benefit from automatic stimulation routing is Pulmonary Vein Isolation Validation.

In some embodiments, the processor may further use the sensed ECG signals to specify in real-time, using signal processing, the location of a focal or a reentrant arrhythmogenic tissue site, or the results of such testing at each location from which analysis was attempted. The location as well as monitored EP parameters at the location may be indicated and displayed to a user on an anatomical map (that the processor may generate using the disclosed workflow) using visual indications, such as enumerated tags and/or colors. In another embodiment, the processor is further configured to visually indicate qualitative or quantitative results obtained from pacing at each paced intracardiac location to a user on the EP map.

Typically, the processor is programmed in software containing a particular algorithm that enables the processor to conduct each of the processor related steps and functions outlined above.

The disclosed automatic pacing technique may increase the probability of a cardiac pacing procedure succeeding in identifying a source of an arrhythmia while at the same time decrease the work load experienced by the physician performing the procedure.

System Description

FIG. 1 is a schematic, pictorial illustration of a cardiac 3D navigation, electrophysiological (EP) diagnostics system 20, comprising a radiofrequency (RF) ablation sub-system, in accordance with an embodiment of the present invention. System 20 may be configured to stimulate and analyze substantially any EP parameter or combinations of such parameters. In the description herein, by way of example, the signals analyzed are assumed to be intra-cardiac and/or extra-cardiac (body surface) ECG potential-time relationships. In order to fully characterize such relationships, the signals at various locations need to be referenced in time to each other, such as is done, for example, during generating a local activation time (LAT) map. The time referencing is accomplished by measuring relative to a reference-time (e.g., instance), such as the beginning of each QRS complex of an ECG reference signal (i.e., the beginning of every heartbeat). A method for generating a LAT map is described in U.S. Pat. No. 9,050,011, cited above.

In the following description system 20 stimulates (i.e., paces) heart 34 using a pacing and ablating probe 24. System 20 measures resulting electrical activity of a heart 34, using probe 24 itself and/or using an additional probe 14. A distal end 32 of probe 24 is assumed to have electrodes 22. The measured signals are used, among other usages, for creating a LAT map of at least part of wall tissue of heart 34 of a patient 26.

Typically, probe 24 comprises a mapping catheter which is inserted into the body of patient 26 during a mapping procedure performed by a physician 28 using system 20. As seen in inset 25, the procedure embodied in FIG. 1 uses an M1-M2 bi-polar electrode pair configuration of probe 24 for the pacing (i.e., for EP stimulating). In addition to stimulating and sensing of EP signals, electrode M1 is configured to subsequently RF ablate tissue site found as arrhythmogenic (be it focal or reentrant) using RF power source 33.

During the procedure patient 26 is assumed to be attached to a grounding electrode (i.e., ground patch) 23. In addition, electrodes 29 are assumed to be attached to the skin of patient 26, in the region of heart 34.

System 20 may be controlled by a system processor 40, comprising a processing unit 42 communicating with a memory 44. In some embodiments, a memory 44, which is included in system processor 40, stores an EP map 62 of at least part of the wall tissue of heart 34 of patient 26. Additionally or alternatively, memory 44 may store maps of other patients. Moreover, any other processor (i.e., not necessarily part of system 20) that comprises a memory may store one or more such maps. Processor 40 is typically mounted in a console 46, which comprises (a) a patient interface unit 43 to which all the catheters connect, and (b) a workstation having operating controls 38, typically including a pointing device 39 such as a mouse or trackball, that physician 28 uses to interact with the processor.

Figure 2:
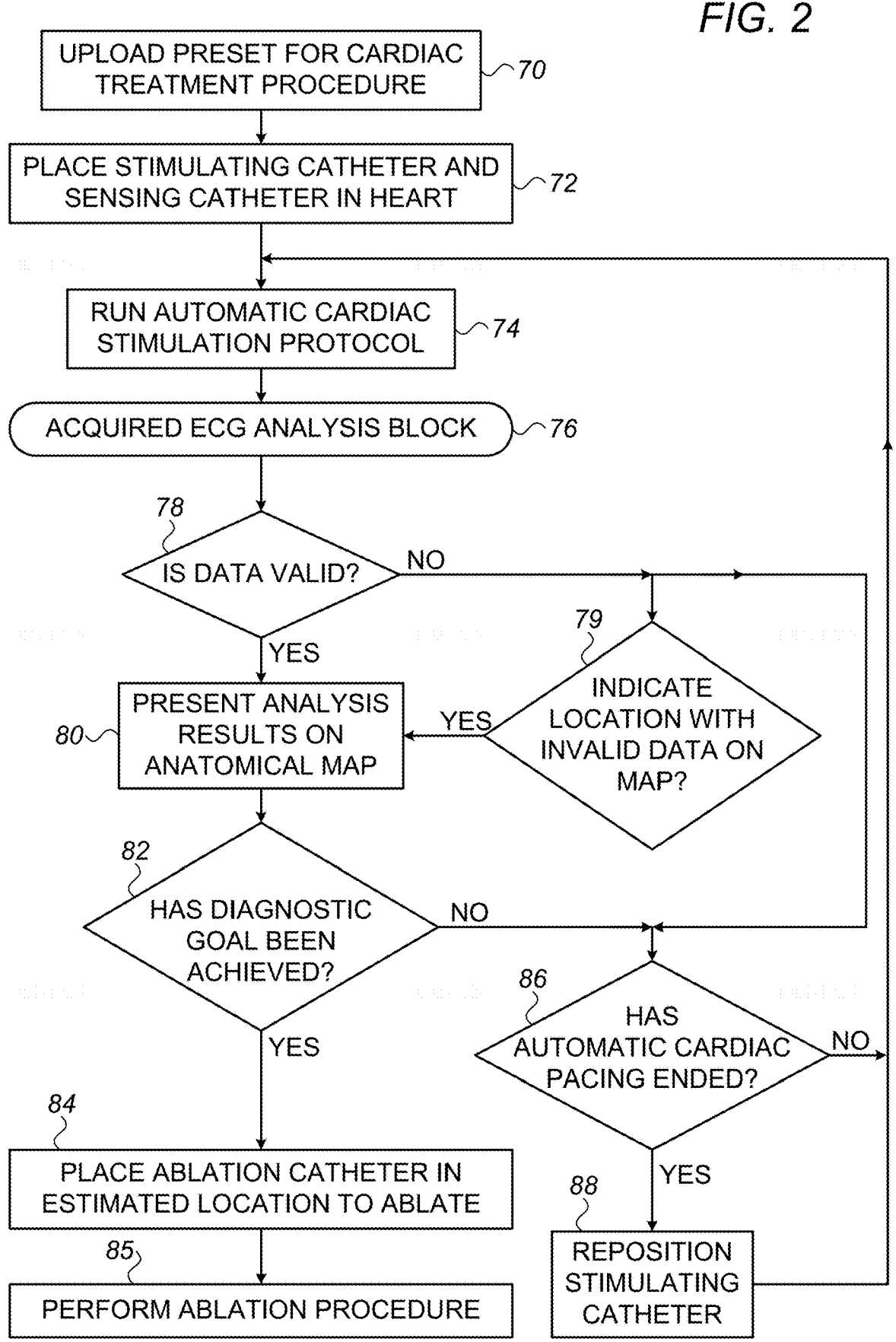
FIG. 2 is a flow chart that schematically illustrates a goal-driven workflow for cardiac arrhythmia treatment using catheters, in accordance with an embodiment of the present invention.

Processor 40 (specifically processing unit 42) runs software, comprising a probe tracker module 30, an ECG module 36 comprising an arrhythmia analysis module, and a graphical user interface (GUI) 35, to operate system 20 and/or to graphically analyze and present results (using EP map 62 stored in memory 44) from the disclosed automated heart pacing workflow described in FIG. 2 so as, for example, to identify sources of an arrhythmia.

In an embodiment, ECG module 36 is coupled to receive electrical signals from electrodes 22 and electrodes 29. The module is configured to analyze the electrical signals and may present the results of the analysis in a standard ECG format, typically a graphical representation moving with time, on display 48.

Probe tracker module 30 typically tracks the location of distal end 32 of probe 24, within the heart of patient 26. The tracker module may use any method for location tracking probes known in the art. For example, module 30 may operate a magnetic-field based location tracking sub-system. (For simplicity components of such sub-system are not shown in FIG. 1.)

Alternatively or additionally, tracker module 30 may track probe 24 by measuring impedances between electrode 23 and electrode 22, as well as the impedances to other electrodes which may be located on the probe. (In this case electrodes 22 may provide both ECG and location tracking signals.) The Carto3® system produced by Biosense-Webster (Irvine, Calif.) uses both magnetic field location tracking and impedance measurements for location tracking.

Using tracker module 30 processor 40 is able to measure locations of distal end 32. In addition, using both tracker module 30 and ECG module 36 the processor is able to measure locations of the distal end, as well as LATs of electrical signals detected at these particular locations.

Results of the operations performed by processor 40 are presented to physician 28 on a display 48, which typically presents a graphic user interface to the physician, a visual representation of the ECG signals sensed by electrodes 22, and/or an image or map of heart 34 while it is being investigated. In an embodiment, GUI 35 present to the physician an EP map updated with one or more locations on the map where an identified arrhythmia originated from or propagated through, as well as information from each location tested by the methods of this invention. The software may be downloaded to processor 40 in electronic form, over a network, for example, or it may, alternatively or additionally, be provided and/or stored on non-transitory tangible media, such as magnetic, optical, or electronic memory.

Goal-Driven Workflow for Cardiac Arrhythmia Treatment

FIG. 2 is a flow chart that schematically illustrates a goal-driven workflow for cardiac arrhythmia treatment using catheters, in accordance with an embodiment of the present invention. The example brought in FIG. 2 is valid for a reentrant type of arrhythmia in question, whereas the disclosed workflow may use other parameters for diagnosing other types of arrhythmia. The algorithm according to the presented embodiment carries out a process that begins with physician 28 uploading a preset (e.g., an automatic protocol) for cardiac pacing procedure, at an uploading step 70. A schematic summary of such protocol, brought by way of example for use with reentrant atrial flutter, is shown in table I, and is further described below.

TABLE I

| Parameter of Automated workflow | Value |
| --- | --- |
| Catheter locations | Pacing and ablation probe 24 Sensing probe 14 |
| Define stimulation sequence and parameters | Electrodes M1-M2 of probe 24 |
| Select parameters of interest | PCL PPI minus TCL (PPI − TCL) |
| Maneuver validation criteria | All sensed intracardiac signals reach PCL value or stable values within 5 msec of PCL (capture achieved) |
| Desired Goal | 0 <= PPI − TCL < 30 Concealed Fusion |
| ECG signals acquisition, annotation and analysis | CL calculation on all EGMs PPI − TCL Concealed Fusion evaluation |
| Presentation of parameters indication upon anatomical map | Visual indications according to PPI − TCL values overlaid on an anatomical map |

PCL, PPI and TCL are defined as:

TABLE II

| PCL | Paced Cycle Length |
| --- | --- |
| PPI | Post-Pacing Interval |
| TCL | Tachycardia Cycle Length |

The physician may change parameter values in the uploaded protocol and save the changed preset as a new protocol. As noted above, parameters that may be changed include catheter positions, pacing sequence of stimulation that includes waveforms, as well as acceptance criteria for automated ECG data validation—which otherwise a physician has to decide upon case by case. Physician 28 then positions stimulating and sensing probe 24 and additional (sensing) probe 14 inside heart 34, at a probe (e.g., catheter) positioning step 72.

Next, physician 38 runs the automatic cardiac pacing protocol, at an automatic pacing step 74, at which probe 24 stimulates cardiac locations and probe 24 and/or probe 14 sense resulting ECG signals. During pacing, processor 40, which runs the disclosed automated work flow, applies an algorithm to automatically determine whether pacing is successfully achieved, at a pacing analysis step 76.

In an embodiment, processor 40 annotates the sensed ECG signals and analyzes the annotated signals using, for example, a criterion in which such ECG signals, sensed from all relevant electrodes of probe 24 and/or probe 14, must show a cycle length that is within typically several msec of the PCL. Such criteria ensure that pacing has indeed "taken over" the naturally occurring electrical activity of heart 34 at the paced location, a necessary condition for the pacing maneuver to become valid.

If an analyzed ECG signal has too large a cycle length (CL), i.e., from table I, CL>PCL+5 mSec, processor 40 automatically classifies the sensed ECG data set as invalid, at a data validation check step 78. Note that without the disclosed automated workflow, a physician would have to manually approve each sensed ECG data set as valid. If ECG data is found invalid, e.g. if there is no capture, the algorithm may mark invalid data locations on the anatomical map, at a marking decision step 79. In any case, the algorithm of FIG. 2 also goes from step 78 directly to step 86.

If data is found valid at step 78, processor 40 generates and presents results of the automated pacing, such as an indication of the paced location and a calculated PPI-TCL value, on an anatomical map of the heart by, for example, positioning a temporary validation tag on the map, at a results-analysis presentation step 80. In an embodiment, the algorithm identifies a direction that leads towards lower (i.e., closer to zero) PPI-TCL values, if such recommendation is required, and recommend a location in this direction as a next pacing location, by overlaying the recommended direction on the anatomical map.

A calculated stimulation resulting PPI-TCL value at a given paced location, which is within the range of [0, 30] msec is highly indicative of the location of an aberrant tissue site. For example, a LAT value is directly proportional to the distance of a mapping electrode to a location of a reentrant circuit. In analysis step 76, processor 40 also calculates PPI and TCL. Assuming ECG data is found valid, the respective difference between the PPI and TCL is therefore used as an indication of physical proximity of probe 24 to an aberrant tissue site. Using the above LAT criterion, processor 40 may diagnose the location as arrhythmogenic, at a diagnostic goal checking step 82. If the location is found arrhythmogenic, processor 40 updates the anatomical map, for example by automatically visually indicating (e.g., tagging, coloring) a location over map as candidate location for ablation, as part of step 78. The physician then places the ablation catheter at the estimated location to ablate, at an ablation catheter positioning step 84.

An additional way to determine a cardiac site as a source of a reentrant arrhythmia is the autodetection of a concealed fusion in the ECG signal from that site, also applied at diagnostic goal checking step 82. Concealed fusion is defined, for example, by G. D. Veenhuyzen et al. in "Diagnostic Utility for Supraventricular Tachycardia," Indian Pacing Electrophysiology Journal, 8(1): pages 51-65, (2008).

The disclosed process then moves to instruct performing RF ablation at the visually indicated location, using electrode Ml, at an ablation procedure step 85.

As noted above, if sensed ECG data is found in step 78 as invalid the process goes to a checking step 86, in which processor 40 checks if the automatic pacing protocol was performed in its entirety. If the answer is negative, the process loops back to step 74, to continue pacing. If the answer is positive, the algorithm concludes that pacing the given site was exhausted and instructs moving pacing (i.e., stimulating) probe 24 to another tissue location, at a repositioning stimulating catheter step 88.

If at step 82, the diagnostic goal has not been achieved yet (e.g., the location is found normal), then processor 40 applies checking step 86 as above, and instructs repositioning step 88 as necessary.

The example flow chart shown in FIG. 2 is chosen purely for the sake of conceptual clarity. Additional steps may be typically performed, such as physician 28 initially anatomically mapping relevant parts of heart 34 (e.g., using fast anatomical mapping (FAM) procedure) to obtain an anatomical map. The criteria may vary with the type of pacing procedure and respective clinical goals. In some embodiments, the disclosed automated workflow is configured to accept additional inputs, such as temperature and contact force readings.

In another embodiment, an existence of a reentrant circuit is identified automatically by performing an overdrive stimulation (pacing the heart at a rate higher than the tachycardia rate) from various electrodes inside the target chamber until clear stable fusion signal is achieved and automatically identified, for example, using a CARTO® system (produced by Biosense-Webster). The sensed ECG signals are annotated and analyzed in real time using currently existing algorithms in the CART® system.

Figure 3:
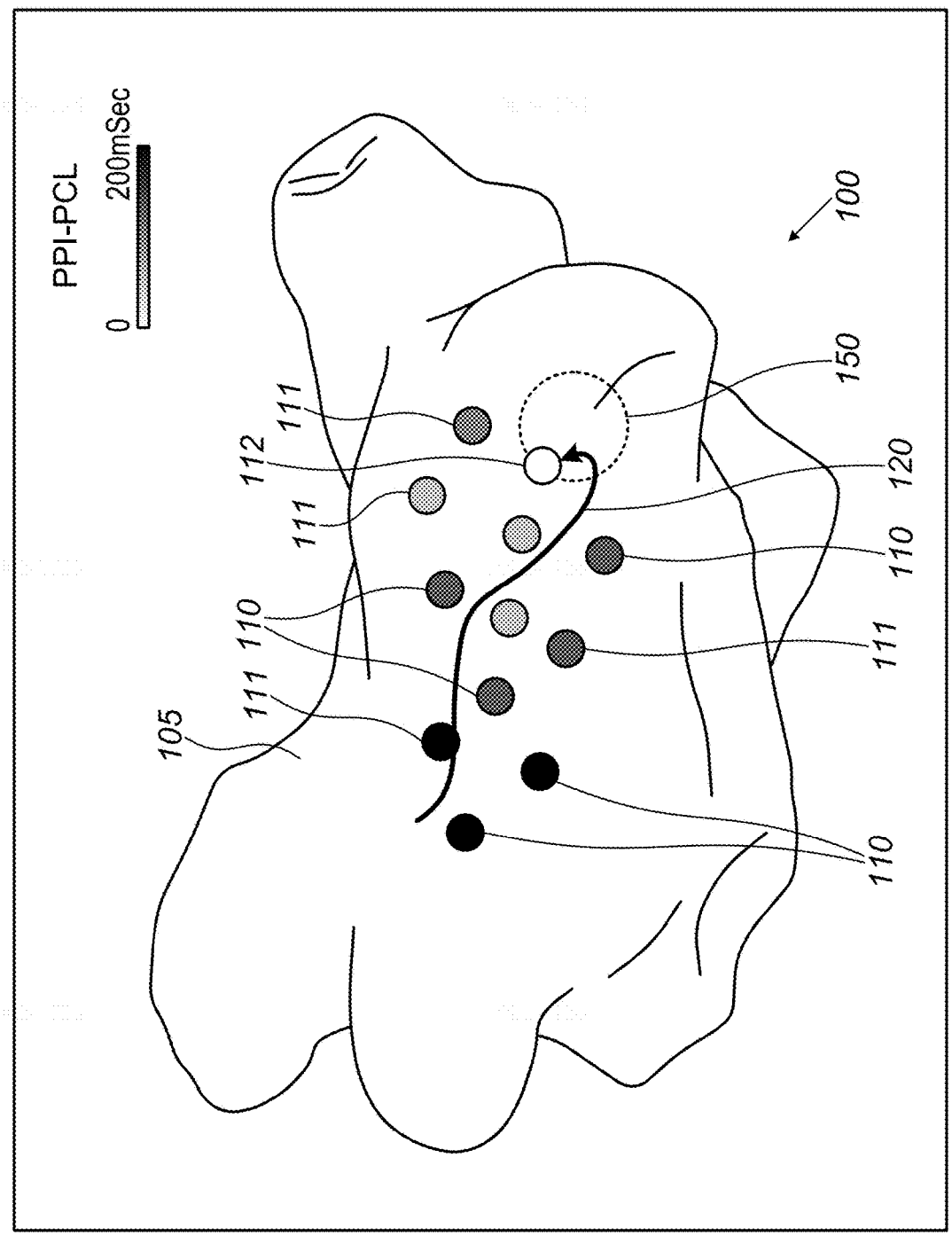
FIG. 3 is a schematic, pictorial volume rendering of an arrhythmia location guide map of a left atrium, automatically generated by a processor employing the automated workflow described in FIG. 2, in accordance with an embodiment of the present invention.

FIG. 3 is a schematic, pictorial volume rendering of an arrhythmia location guide map 100 of a left atrium, automatically generated by a processor 40 employing the automated workflow described in FIG. 2, in accordance with an embodiment of the present invention. FIG. 2 shows analyzed ECG signals 110, 111 and 112, overlaid on anatomical map 105 of the left atrium of a patient. Signals 110 were found (in step 78 of FIG. 2) by processor 40 as valid, whereas signals 111 were found by processor 40 as invalid (but are still shown in FIG. 3 to explain the decision-making process that the processor 40 applies). As seen, using a LAT criterion described in analysis step 76 of FIG. 2, processor 40 constructs a path 120 that guides the physician towards a potential location of a reentrant circuit 150, which processor 40 subsequently verifies after analyzing ECG signals 112.

An initial pacing location can be chosen by the physician based on a previously obtained EP map or previous patient data that suggests patient's arrhythmia type and its expected location. From there on, the physician may move the catheter in a certain location according to the received indications of PPI-TCL values on arrhythmia guide map 100. In an embodiment, the physician moves the catheter slightly to several directions for the algorithm to find a tendency of the values towards zero. Once several such points were collected by the algorithm, the algorithm can identify a location in a direction that may lead towards lower (i.e., closer to zero) PPI-TCL values, and recommend this location as a next pacing location.

Arrhythmia location guide map 100 that processor 40 generates provides the physician an objective result of the pacing procedure, and saves the physician futile efforts he might otherwise be experiencing in unsuccessfully attempting manually creating and tracking path 120, resulting in diagnostically failed pacing procedure.

Although the embodiments described herein mainly address automated diagnostic workflow for cardiac applications, the methods and systems described herein can also be used in other medical applications, such as in brain surgery, to verify by pacing that no damage is made to certain areas in the brain and to analyze the acquired EEG signals which are indicators of brain activity. Other medical applications that may utilize the disclosed technique are orthopedic surgeries, such as spinal surgeries, to ensure that no neural damage is made to the patient during surgery, or to create a nerve mapping before the surgery begins.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A system, comprising:
a memory, which is configured to store a definition of an automatic cardiac pacing protocol comprising one or more prespecified criteria for validity of the sensed electrocardiogram ECG data preset in the automatic pacing protocol; and
a processor, which is configured to:
receive the stored definition of the automatic cardiac pacing protocol;
automatically control one or more probes in a heart of a patient, in accordance with the automatic pacing protocol, to automatically pace from an intracardiac location and to acquire respective sensed ECG signals;
automatically accept or reject the sensed ECG signals using the automatic cardiac pacing protocol;
based on the one or more prespecified criteria for identification of an arrhythmia, identify or reject the intracardiac location as an arrhythmogenic focus or pathway using the automatic cardiac pacing protocol;
overlay the identified intracardiac location on an electrophysiological (EP) map; and
subsequently identify a new intracardiac location as an arrhythmogenic focus or pathway and overlay the new location on the EP map when pacing again from the new intracardiac location,
wherein the prespecified criteria for validity comprise a criterion in which the sensed ECG signals must show an ECG cycle length (CL) that is within a predetermined length of the paced cycle length (PCL); and
wherein the processor is configured to identify a location as an arrhythmogenic focus or pathway by identifying a location in a direction that leads towards post-pacing interval (PPI) minus tachycardia cycle length (TCL) values closer to zero or lower difference in time lapse values.

2. The system according to claim 1, wherein the definition comprises at least a pacing sequence.

3. The system according to claim 1, wherein the processor is further configured to visually indicate qualitative or quantitative results obtained from pacing at each paced intracardiac location to a user on the EP map.

4. The system according to claim 1, wherein the pacing protocol specifies the one or more criteria for identification of a location as an arrhythmogenic focus or pathway, the criteria comprising one of:
a comparison of tachycardia cycle length (TCL) to post-pacing interval (PPI) in a same ECG signal; and
a comparison of time lapse between pacing signal to a resulting body surface or intracardiac ECG signal with time lapse between one or more following pacing signals and respective resulting body surface or intracardiac ECG signals.

5. The system according to claim 4, wherein the pacing protocol specifies the one or more criteria for validity of the sensed ECG data, comprising comparison of time lapse values.

6. The system according to claim 1, wherein the pacing protocol specifies the one or more criteria for identification of a location as an arrhythmogenic focus or pathway, comprising identifying one or more of (i) concealed fusion and (ii) manifested fusion, in a sensed ECG signal.

7. The system according to claim 1, wherein the processor is configured to measure the intracardiac paced location using a position tracking system.

8. The system according to claim 1, wherein the processor is configured to store the definition of the cardiac pacing protocol by at least one of saving, importing, and exporting of the pacing protocol.

9. The system according to claim 1 wherein the predetermined length is 5 mSec.

10. A computer-implemented method, comprising:
in a processor, receiving a definition of an automatic cardiac pacing protocol comprising one or more prespecified criteria for validity of the sensed ECG data preset in the automatic pacing protocol;
using the processor, automatically controlling one or more probes in a heart of a patient, in accordance with the automatic pacing protocol, to automatically pace from an intracardiac location and to acquire respective sensed electrocardiogram (ECG) signals;
automatically accepting or rejecting the sensed ECG signals using the automatic cardiac pacing protocol;
based on the one or more prespecified criteria for identification of an arrhythmia, identifying or rejecting the intracardiac location as an arrhythmogenic focus or pathway;
overlaying the identified intracardiac cardiac location on an electrophysiological (EP) map; and
subsequently identifying a new intracardiac location as an arrhythmogenic focus or pathway and overlaying the new location on the EP map when pacing again from the new intracardiac location,
wherein the prespecified criteria for validity comprise a criterion in which the sensed ECG signals must show an ECG cycle length (CL) that is within a predetermined length of the paced cycle length (PCL); and
wherein identifying a location as an arrhythmogenic focus or pathway comprises identifying a location in a direction that leads towards post-pacing interval (PPI) minus tachycardia cycle length (TCL) values closer to zero or lower difference in time lapse values.

11. The method according to claim 10, wherein the definition comprises at least a pacing sequence.

12. The method according to claim 10, and comprising visually indicating qualitative or quantitative results obtained from pacing at each paced intracardiac location to a user on the EP map.

13. The method according to claim 10, wherein the pacing protocol specifies the one or more criteria for identification of a location as an arrhythmogenic focus or pathway, the criteria comprising one of:
a comparison of tachycardia cycle length (TCL) to post-pacing interval (PPI) in a same ECG signal; and
a comparison of time lapse between pacing signal to a resulting body surface or intracardiac ECG signal with time lapse between one or more following pacing signals and respective resulting body surface or intracardiac ECG signals.

14. The method according to claim 10, wherein identifying a location as an arrhythmogenic focus or pathway further comprises identifying a location in a direction that leads towards minimal or maximal values of PPI minus-TCL values or minimal or maximal time lapse values, and recommending the location to a user as a next pacing location.

15. The method according to claim 10, wherein the pacing protocol specifies the one or more criteria for validity of the sensed ECG data, comprising a comparison of time lapse values.

16. The method according to claim 10, wherein the pacing protocol specifies the one or more criteria for identification of a location as an arrhythmogenic focus or pathway, comprising identifying one or more of (i) concealed fusion and (ii) manifested fusion, in a sensed ECG signal.

17. The method according to claim 10, and comprising measuring the intracardiac location using a position tracking system.

18. The method according to claim 10 wherein the predetermined length is 5 mSec.

* * * * *